United States Patent
Dean et al.

(10) Patent No.: US 10,758,411 B2
(45) Date of Patent: Sep. 1, 2020

(54) RECIPROCATING SURGICAL TOOL WITH INERTIAL DAMPER

(71) Applicant: Novartis AG, Basel (CH)

(72) Inventors: Joshua Dean, Oceanside, CA (US); Nicholas Max Gunn, Newport Beach, CA (US); Andrew David Johnson, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 48 days.

(21) Appl. No.: 15/889,424

(22) Filed: Feb. 6, 2018

(65) Prior Publication Data
US 2018/0243134 A1      Aug. 30, 2018

Related U.S. Application Data

(60) Provisional application No. 62/464,068, filed on Feb. 27, 2017.

(51) Int. Cl.
*A61F 9/007* (2006.01)
*A61B 17/00* (2006.01)

(52) U.S. Cl.
CPC ............. *A61F 9/00763* (2013.01); *A61B 2017/00544* (2013.01)

(58) Field of Classification Search
CPC ........ A61F 9/00763; A61F 9/00; A61F 9/007; A61B 2017/00544; A61B 2017/320088; A61B 17/32; F16F 7/00
See application file for complete search history.

(56) References Cited

U.S. PATENT DOCUMENTS

| | | |
|---|---|---|
| 5,176,628 A | 1/1993 | Charles et al. |
| 8,038,692 B2 | 10/2011 | Valencia |
| 8,080,029 B2 | 12/2011 | Charles |
| 8,187,293 B2 | 5/2012 | Kirchhevel |
| 8,298,253 B2 | 10/2012 | Charles |
| 8,540,743 B2 | 9/2013 | Auld |
| 9,005,228 B2 | 4/2015 | Underwood |
| 9,095,410 B2 | 8/2015 | Underwood |
| 9,486,360 B2 | 11/2016 | Chon |
| 9,517,161 B2 | 12/2016 | Underwood |
| 9,757,273 B2 | 9/2017 | Heeren |
| 9,924,963 B2 | 3/2018 | Mcdonell |
| 9,974,689 B2 | 5/2018 | Mcdonell |
| 10,251,782 B2 | 4/2019 | Farley |
| 10,369,046 B2 | 8/2019 | Mcdonell |
| 10,555,834 B2 | 2/2020 | Charles |
| 2006/0157310 A1 | 7/2006 | Lee |
| 2007/0185514 A1 | 8/2007 | Kirchhevel |
| 2008/0188881 A1 | 8/2008 | Chon |
| 2011/0295292 A1 | 12/2011 | Hsia |
| 2012/0316490 A1 | 12/2012 | Perkins |
| 2016/0030240 A1 | 2/2016 | Gonenc et al. |

(Continued)

*Primary Examiner* — George J Ulsh

(57) ABSTRACT

A handheld reciprocating surgical tool may contain an inertial damper to counteract the momentum of a diaphragm assembly of the reciprocating surgical tool. A momentum of the inertial damper may be tuned such that the momentum of the inertial damper is comparable in magnitude and opposite in direction to a momentum of the diaphragm assembly. The diaphragm assembly may include a cutting tool. The combined momentum of a diaphragm assembly and the inertial damper may result in a reduced net momentum, which may reduce vibration of the reciprocating surgical tool haptically experienced by a surgeon, thereby improving surgeon comfort.

10 Claims, 6 Drawing Sheets

(56) References Cited

U.S. PATENT DOCUMENTS

2016/0120697 A1 5/2016 Farley
2018/0360660 A1 12/2018 Lopez
2018/0369016 A1 12/2018 Underwood

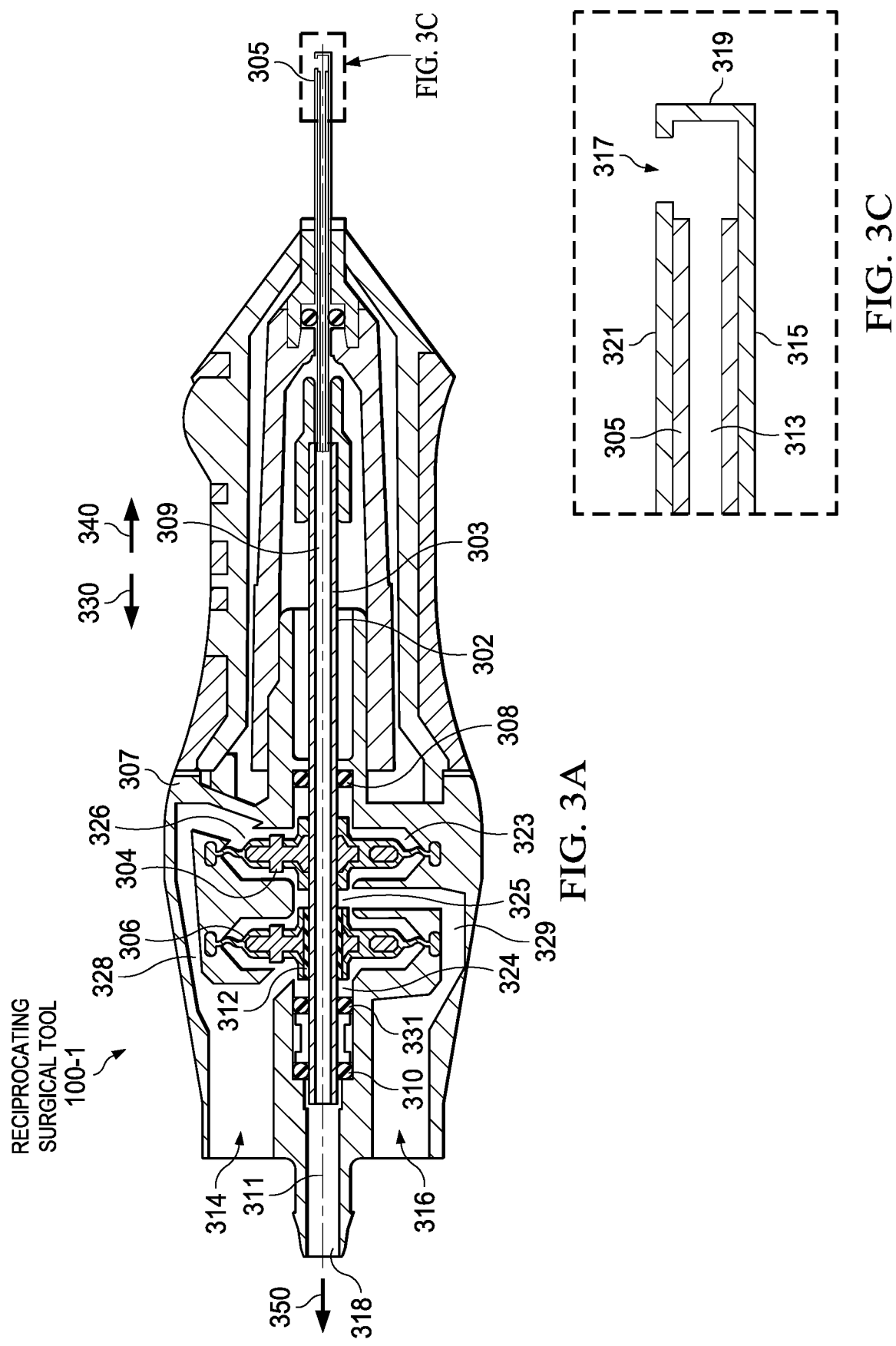

RECIPROCATING SURGICAL TOOL WITH INERTIAL DAMPER

TECHNICAL FIELD

The present disclosure relates to reciprocating surgical tools having an inertial damper, and, more specifically, to vitrectomy probes having an inertial damper. The present disclosure also discloses methods of performing ophthalmic surgery using a reciprocating surgical tool with an inertial damper.

BACKGROUND

Ophthalmic surgery is performed on the eye to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in precision or accuracy of surgical techniques can make a significant difference in the patient's vision after the surgery.

Vitreoretinal surgery, a type of ophthalmic surgery, encompasses various delicate procedures involving internal portions of an eye, such as vitreous humor and the retina. Different vitreoretinal surgeries are used to improve visual sensory performance in the treatment of many eye diseases, including epimacular membranes; diabetic retinopathy; vitreous hemorrhage; macular hole; detached retina; complications of cataract surgery; or other eye diseases.

During vitreoretinal surgery, an ophthalmologist typically uses a surgical microscope to view the fundus in the interior of the eye through the cornea, while surgical instruments that penetrate the sclera may be introduced to perform any of a variety of different procedures. A surgical microscope may provide imaging and optionally illumination of the fundus during vitreoretinal surgery. A patient typically lies supine under the surgical microscope during vitreoretinal surgery and a speculum is used to keep the eye exposed.

Modern ophthalmic surgery, such as vitreoretinal surgery, is typically performed with complex equipment, such as specialized surgical probes; infusion pumps; pneumatic valves; pneumatic pumps; pneumatic compressors; aspirators; illumination sources; cooling fans; lasers; or other equipment. Surgical probes used in vitreoretinal surgery may include reciprocating vitrectomy probes. Some reciprocating vitrectomy probes may use dual pneumatic actuation inputs that enable control of a duty-cycle of a reciprocating cutter contained in the surgical probe. Surgical probes operating at relatively high cutting rates may generate significant vibration during use, which may be unpleasant and adversely affect working conditions for a surgeon.

SUMMARY

The present disclosure discloses a reciprocating surgical tool for use in ophthalmic surgery. The reciprocating surgical tool may include a housing body, a first channel formed in the housing body, a second channel formed in the housing body, and a diaphragm assembly having a first mass. The diaphragm assembly may include a first diaphragm and a surgical cutter. The diaphragm may be reciprocated in a first direction and a second direction in response to alternating pneumatic pressures applied to the first diaphragm via the first channel to cause the diaphragm assembly to be displaced in the first direction and via the second channel to cause the diaphragm assembly to be displaced the second direction opposite the first direction. The diaphragm assembly may have a first momentum when being displaced in the first direction and the second direction. The reciprocating surgical tool may also include an inertial damper. The inertial damper may be reciprocated in the first direction and the second direction in response to the alternating pneumatic pressures applied to the inertial damper via the first channel to cause the inertial damper to be displaced in the second direction and via the second channel to cause the inertial damper to be displaced in the first direction. The inertial damper may have a second momentum less than or equal to the first momentum in magnitude when being displaced in the first direction and the second direction, and the second momentum and the first momentum may be diametrically opposite.

Alternating pneumatic pressure may be supplied from an ophthalmic surgical system. The ophthalmic surgical system may include a dual-channel pneumatic actuator configured to provide the pneumatic pressure pulses to the first channel and to the second channel independently of each other and an aspiration system configured to provide a vacuum to passage extending through the surgical cutter. The reciprocating surgical tool may be a handheld surgical tool. The handheld surgical tool is a vitrectomy probe. The surgical cutter may operate at a rate of up to 1,000 cutting cycles per second. The inertial damper may include a free mass that is configured to reciprocate in an enclosed channel formed in the housing body. The sliding mass damper may include a second diaphragm that is the same size as the first diaphragm. The surgical cutter may be fixed to the first diaphragm along a central axis thereof. The inertial damper may include a second diaphragm that is smaller in size than the first diaphragm. The inertial damper may include a metallic portion having a second mass that is less than or equal to the first mass.

The scope of the disclosure also includes a method for operating a reciprocating surgical tool. The method may include reciprocating the diaphragm assembly of the reciprocating surgical tool in response to alternating pneumatic pressure pulses. The diaphragm assembly may form a primary mass and having a first momentum when moving in each of a first direction and a second direction, opposite the first direction, of the reciprocating movement. The method may also include reciprocating the inertial damper in response to the alternating pneumatic pressure pulses. The inertial damper may have a second momentum that is less than or equal to the first momentum when moving in each of the first direction and the second direction of the reciprocating movement. The first momentum and the second momentum may be diametrically opposed.

The diaphragm assembly may include a first diaphragm and a surgical cutter. Reciprocating the diaphragm assembly may include applying a first pneumatic pressure pulse of the pneumatic pressure pulses to a first side of the first diaphragm to cause displacement of the first diaphragm in second direction and applying a second pneumatic pressure pulse of the pneumatic pressure pulses to a second side of the first diaphragm to cause displacement of the first diaphragm in the first direction. The inertial damper may include a second diaphragm. Reciprocating the inertial damper may include applying the first pressure pulse to a second side of the second diaphragm to cause displacement of the second diaphragm in the first direction and applying the second pressure pulse to a first side of the first diaphragm to cause displacement of the second diaphragm in the second direction. The reciprocating surgical tool may be a vitrectomy probe. The diaphragm assembly may include a surgical cutter, and the surgical cutter may operate at a rate of up to 1,000 cutting cycles per second. Reciprocating the inertial damper may include reciprocating a free mass in an enclosed channel formed in a housing body of the reciprocating surgical tool. The diaphragm assembly may include a first diaphragm and a surgical cutter fixed to the first diaphragm along a central axis thereof. The second diaphragm may be smaller in size than the first diaphragm. The secondary mass is less than or equal to the primary mass It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and the associated features and advantages described herein, reference is now made to the following description, taken in conjunction with the accompanying drawings, which may not be drawn to scale and, in which like numerals refer to like features.

FIG. 3A is a schematic diagram of an example reciprocating surgical tool containing a diaphragm inertial damper;

FIG. 3C is a detail view of a distal end of the surgical tool shown in FIG. 3A.

DETAILED DESCRIPTION

Figure 1:
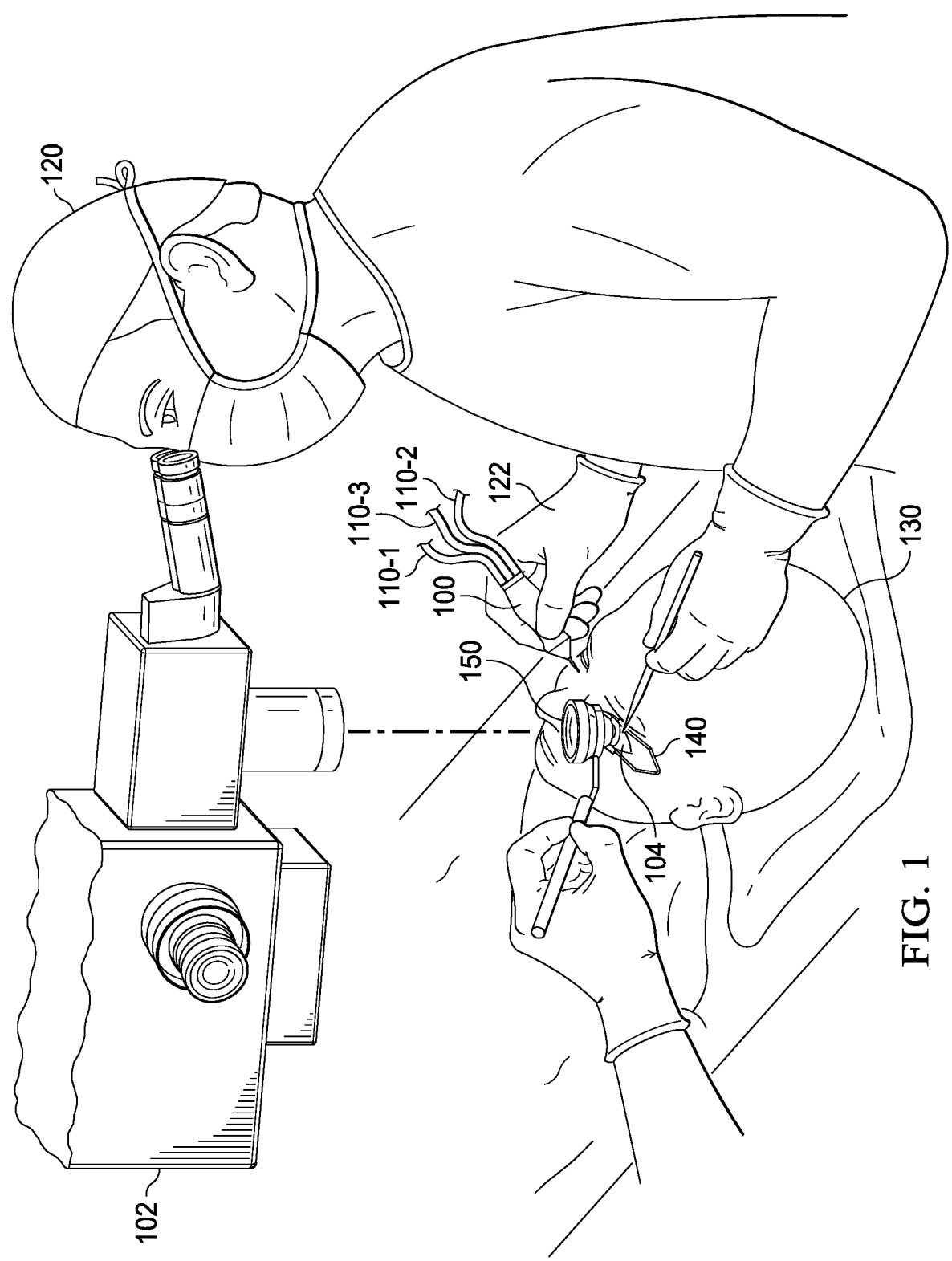
FIG. 1 shows a surgeon performing an ophthalmic surgery on an eye of a patient using a reciprocating surgical tool with an inertial damper.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure is fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Throughout this disclosure, a hyphenated form of a reference numeral refers to a specific instance of an element and the un-hyphenated form of the reference numeral refers to the element generically or collectively. Thus, as an example (not shown in the drawings), device "12-1" refers to an instance of a device class, which may be referred to collectively as devices "12" and any one of which may be referred to generically as a device "12". In the figures and the description, like numerals are intended to represent like elements.

A reciprocating surgical tool that contains a reciprocating primary mass may be implemented with an inertial damper. For instance the inertial damper may be used in a surgical tool that is a vitrectomy probe, in which a reciprocating cutter, representing a reciprocating primary mass, is operable to cause small portions of the vitreous of a patient's eye to be cut away and removed. One example of a vitrectomy probe, which may be used with some implementations described herein, is the ULTRAVIT® surgical probe produced by Alcon Laboratories, Inc., located at 6201 South Freeway, Fort Worth, Tex. 76134. In general, vitrectomy probes may operate at a relatively high cutting rate. The disclosure is not limited to vitrectomy probes or high-cutting-rate vitrectomy probes, however. In some implementations, an inertial damper as described herein may be used with lower-cutting-rate vitrectomy probes, high-cutting-rate vitrectomy probes operating at lower cutting rates, or other surgical tools for use in vitreoretinal or other ophthalmic surgery in which a primary mass or other reciprocating component reciprocates at any of a variety of reciprocation rates. Further, the scope of the present disclosure is not limited to ophthalmology. Rather, the principles described herein may be applicable to other medical fields.

An inertial damper as described herein may contain a secondary mass that counter-reciprocates to mechanically counteract the momentum of a primary mass in a reciprocating surgical tool. Although the disclosure is not so limited, in some implementations, if a primary mass in a reciprocating surgical tool is pneumatically actuated using dual pneumatic actuation inputs, a secondary mass in the inertial damper may be actuated by the same dual pneumatic actuation inputs, but in the opposite direction of motion so as to dampen the momentum of the primary mass. In this manner, the overall vibration generated by a reciprocating surgical tool with an inertial damper and haptically perceived by a surgeon holding the reciprocating surgical tool may be diminished, which is desirable.

Accordingly, the disclosed reciprocating surgical tools contain an inertial damper, which may ameliorate any negative effects of reciprocation, such as vibration that is imparted to the surgeon operating the reciprocating surgical tool as well as vibration that is transmitted to the patient. The reciprocating surgical tools with an inertial damper disclosed herein may be used at relatively high reciprocation rates, for example, when vitrectomy probes are operated at high cutting rates. The vibration of the reciprocating surgical tool may be perceived as a negative effect and may adversely affect working conditions for a surgeon using the reciprocating surgical tool.

One manner in which a reciprocating surgical tool 100 may be used is illustrated in FIG. 1, in which a surgeon 120 is performing an ophthalmic surgery on an eye 104 of a patient 130 using a reciprocating surgical tool 100 containing an inertial damper as disclosed herein. In FIG. 1, the eye 104 has been exposed using a speculum 140 and a contact lens 150 is held in place on the eye 104 and visually aligned with a surgical microscope 102 to facilitate visualization of inner structures of the eye 104. The surgeon 120 utilizes the reciprocating surgical tool 100 to perform surgery on inner structures of the eye 104.

For example, when the reciprocating surgical tool 100 is a vitrectomy probe, then the surgeon 120 may use the reciprocating surgical tool 100 to remove the clear, gel-like vitreous that normally fills the interior of the eye 104, taking care to remove substantially only the vitreous, while avoiding interaction with nearby eye structures, such as the retina, that are extremely sensitive to physical contact, including mechanical action of an instrument. The surgeon 120 may also desire to remove the vitreous from the eye 104 as quickly as possible so as to limit exposure of the retina to the light used to visualize the vitreous, which may be potentially damaging at excessive levels. The stability of the surgeon's hand 122 and the surgeon's ability to direct the reciprocating surgical tool 100 with millimeter or sub-millimeter precision may play a significant role in the success of the vitrectomy or the success of the vitreoretinal surgery.

However, if the surgeon were using a different reciprocating surgical tool that did not contain an inertial damper according to the disclosures herein, a net mechanical vibration would be generated and might be haptically perceived at the surgeon's hand 122, such as by his or her fingertips. The vibration might distract the surgeon 120, making it more difficult to perform the surgery, and may have other negative effects, such as causing fatigue or discomfort. Further, such vibrational energy may be transmitted to ocular tissues and may result in injury to the eye 104.

In contrast, when the surgeon 120 is using the reciprocating surgical tool 100 with an inertial damper as disclosed herein, the level of vibration generated may be substantially reduced. For example, some overall vibration may still be generated even when the inertial damper is present and operating, but the overall vibration will have a lower amplitude than mechanical vibrations in a reciprocating surgical tool without an inertial damper. As a result, the vibration from the reciprocating surgical tool 100 with an inertial damper may be haptically imperceptible by the surgeon 120, or may be haptically perceived as an insignificant vibration by the surgeon 120. The surgeon 120 may experience a similar reduction in haptic perception of mechanical vibrations when the reciprocating surgical tool 100 is a type of surgical tool other than a vitrectomy probe and/or when the surgeon 120 is performing an ophthalmic surgery other than a vitrectomy or vitreoretinal surgery.

As illustrated in FIG. 1, the reciprocating surgical tool 100 is shown in a configuration that is compatible with dual pneumatic actuation inputs. Accordingly, the reciprocating surgical tool 100 is shown connected to a plurality of tubes 110-1, 110-2, and 110-3. In the implementation shown in FIG. 1, two exemplary tubes 110-1 and 110-2 may represent the dual pneumatic actuation inputs that provide a pressurized gas, such as compressed air or another gas, to the reciprocating surgical tool 100 (see also FIGS. 2A, 2B, 2C, 2D, 3A, and 3B) to actuate reciprocation of a primary mass in a coordinated manner. Although reference is made to compressed air in the following description, it will be understood that another gas may be substituted for the compressed air in various implementations. The coordination of the pressurized gas supply to the tubes 110-1, 110-2 may be controlled by an external surgical device (not shown), for example, a surgical device containing corresponding pneumatic actuators to alternate pressure pulses to the tubes 110-1, 110-2. Thus, a first tube 110-1 may provide compressed air to actuate movement of the primary mass in one direction, while a second tube 110-2 may provide compressed air to actuate movement of the primary mass in an opposing direction, in order to generate a reciprocating action of the primary mass. Additionally, the tubes 110-1 and 110-2 may actuate counter-reciprocation of the secondary mass (e.g. the inertial damper) of the reciprocating surgical tool 100 (such as depicted in FIGS. 2A, 2B, 2C, 2D, 3A, and 3B). Furthermore, a third tube 110-3 may be used to apply a vacuum through a central opening of the reciprocating surgical tool 100 in order to remove material from the eye. For example, the third tube 110-3 may be used to remove material that has been cut away during the surgical procedure. Accordingly, the third tube 110-3 (also referred to as an aspiration line) may be connected to a vacuum pump that provides a certain amount of underpressure, which may be regulated for a desired aspiration rate of the removed material during cutting, for example. In one example, when the reciprocating surgical tool 100 is a vitrectomy probe, the underpressure (or vacuum) may be regulated by the surgeon to achieve a desired aspiration rate during a vitrectomy.

Although reciprocating surgical tool 100 is described in detail in FIGS. 2A, 2B, 2C, 3A, and 3B as using a pneumatic actuator with two compressed air channels, other types of pneumatic actuators may be used in different implementations. For example, the methods and implementations described herein may be used with single channel pneumatic actuators having a spring-mechanism for the return stroke (see FIG. 2D), which may be used with two external tube connections 110 (a single compressed air tube and an aspiration tube).

As shown FIG. 1, the reciprocating surgical tool 100 may include inertial damping, as disclosed herein, and may internally counteract the mechanical vibration generated during the reciprocating operation of the reciprocating surgical tool 100. The inertial damping implemented within the reciprocating surgical tool 100 may involve a secondary mass included within the reciprocating surgical tool 100 that counter-reciprocates when the cutting tool reciprocates, as will be described in further detail below. In other words, the secondary mass reciprocates exactly one-half cycle out of phase with a primary mass (e.g., a cutting tool) to mechanically counteract the momentum of the primary reciprocating mass of the reciprocating surgical tool 100. The mass of the secondary mass may be comparable to the primary mass. Because the inertial damping system, as disclosed herein, may be mechanically integrated with reciprocating surgical tool 100, no external operational or control input is typically provided by the user, and the inertial damping system is automatically actuated by the same air channel and compressed air supply that actuates the cutting tool within the reciprocating surgical tool 100, as will be described below in further detail.

Figure 2A:
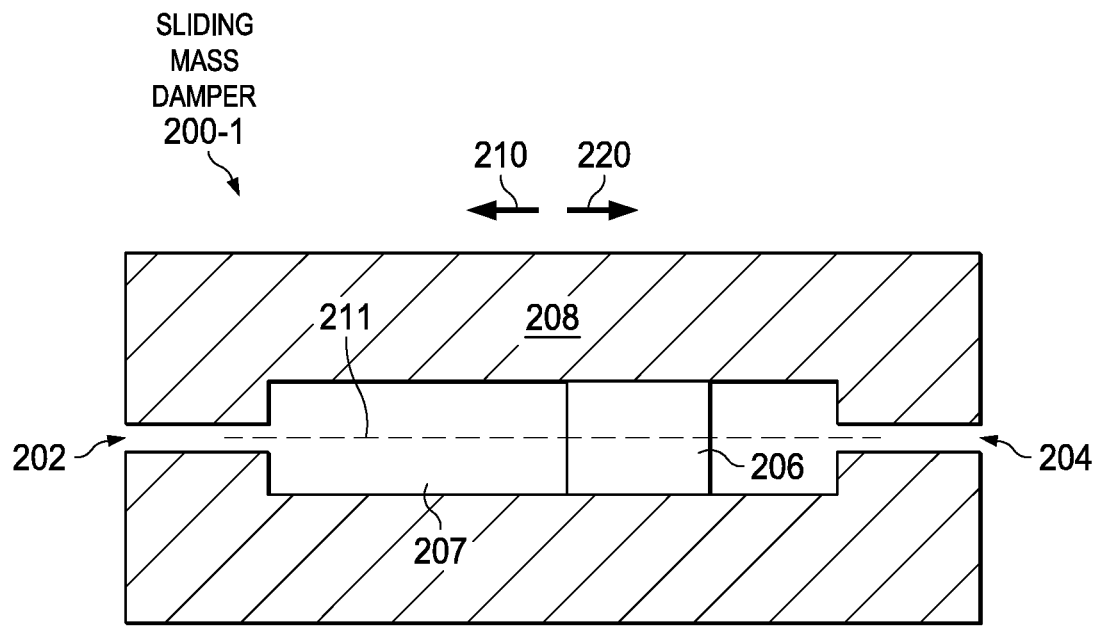
FIG. 2A is schematic diagram of an example sliding mass damper.

FIG. 2A illustrates selected elements of an example of a sliding mass damper 200-1, which may be used as the inertial damper in a reciprocating surgical tool, such as the reciprocating surgical tool 100 shown in FIG. 1. FIG. 2A is a schematic cross-sectional diagram and is not drawn to scale or perspective. The sliding mass damper 200-1 in FIG. 2A contains a housing body 208 having a first channel 202 and a second channel 204 formed therein, as well as a secondary mass 206.

In FIG. 2A, the housing body 208 may be a solid body made of a material, such as a metal; a polymer; a ceramic; any combinations thereof; or any other desired or suitable material. The housing body 208 may be integrally formed with or located within a reciprocating surgical tool 100. As shown in sliding mass damper 200-1, the housing body 208 contains a first channel 202 and a second channel 204 that are aligned with each other. In some implementations, the first channel 202 and the second channel 204 may be formed collinearly within the housing body 208. As depicted in FIG. 2A, the first channel 202 and the second channel 204 are collinearly arranged along a centerline of symmetry 211 in the housing body 208 of the sliding mass damper 200-1. The first channel 202 and the second channel 204 are located at a first end and a second end, respectively, of a central chamber 207. In some implementations, the first channel 202 and the second channel 204 may be cylindrical channels, while other forms and geometries for the first channel 202 and the second channel 204 may be used in various implementations. The first channel 202 and the second channel 204 may be independently connected to respective sources of compressed air, such as tubes 110-1 and 110-2 described above with respect to FIG. 1, such that dual actuation inputs may be provided to the sliding mass damper 200-1.

In FIG. 2A, the first channel 202 and the second channel 204 are in fluid communication with the central chamber 207, which is formed in the housing body 208 and in which the secondary mass 206 is able to reciprocate back and forth as a free mass in a first direction 210 and a second direction 220 opposing the first direction 210. When compressed air is applied to the central chamber 207 via the first channel 202, the secondary mass 206 will move in the second direction 220. When compressed air is applied to the central chamber 207 via the second channel 204, the secondary mass 206 will move in the first direction 210. As shown, sliding mass damper 200-1 is contemplated for use with dual pneumatic actuation inputs that are externally regulated and controlled. It is noted that sliding mass damper 200-1 may be dimensioned to handle various ranges of pressure and flow rates of the compressed air.

The sliding mass damper 200-1 may further contain additional features that are not illustrated. In some implementations, the sliding mass damper 200-1 may contain a fastener, a guide, or other mechanism used to insert or to retain the secondary mass 206 in housing body 208. It is noted that when the secondary mass 206 is cylindrical, in some implementations, a mechanism, such as a channel or a slot, may be used to prevent rotation of the secondary mass 206 about the centerline of symmetry 211.

An interface exists wherever the secondary mass 206 is in contact with an inner surface of the central chamber 207. In some implementations, the interface may be a low-friction interface with sufficient cooling and/or lubrication to support reciprocation of the secondary mass 206 at a reciprocating frequency of up to 1,000 cycles per second. For example, an outer surface of the secondary mass 206 or an inner surface of the central chamber 207, or both, may be coated with a low-friction material. For example, an outer surface of the secondary mass 206 or an inner surface of the central chamber 207, or both may be coated with polytetrafluoroethylene (PTFE) or other material exhibiting a low coefficient of friction.

Typically, the secondary mass 206 will have a mass less than or equal to, or about the same mass, as a primary mass (not shown) in the reciprocating surgical tool 100 containing the sliding mass damper 200-1. In order to control the size of the sliding mass damper 200-1, the secondary mass 206 may be formed from a more dense material than the primary mass. For example, the size of the sliding mass damper 200-1 may be reduced by forming the secondary mass 206 from a dense material, e.g., a material having a greater density than the primary mass. A material selected to form the secondary mass 206 may be determined based on a desired final size of the secondary mass 206. The sliding mass damper 200-1 may be positioned within the reciprocating surgical tool 100 and the secondary mass 206 may be generally dimensioned and positioned such that, when the secondary mass 206 counter-reciprocates, the secondary mass 206 has a momentum generally opposite that of the primary mass. In this manner, the net momentum and net mechanical vibration of the reciprocating surgical tool 100 is reduced.

Figure 3B:
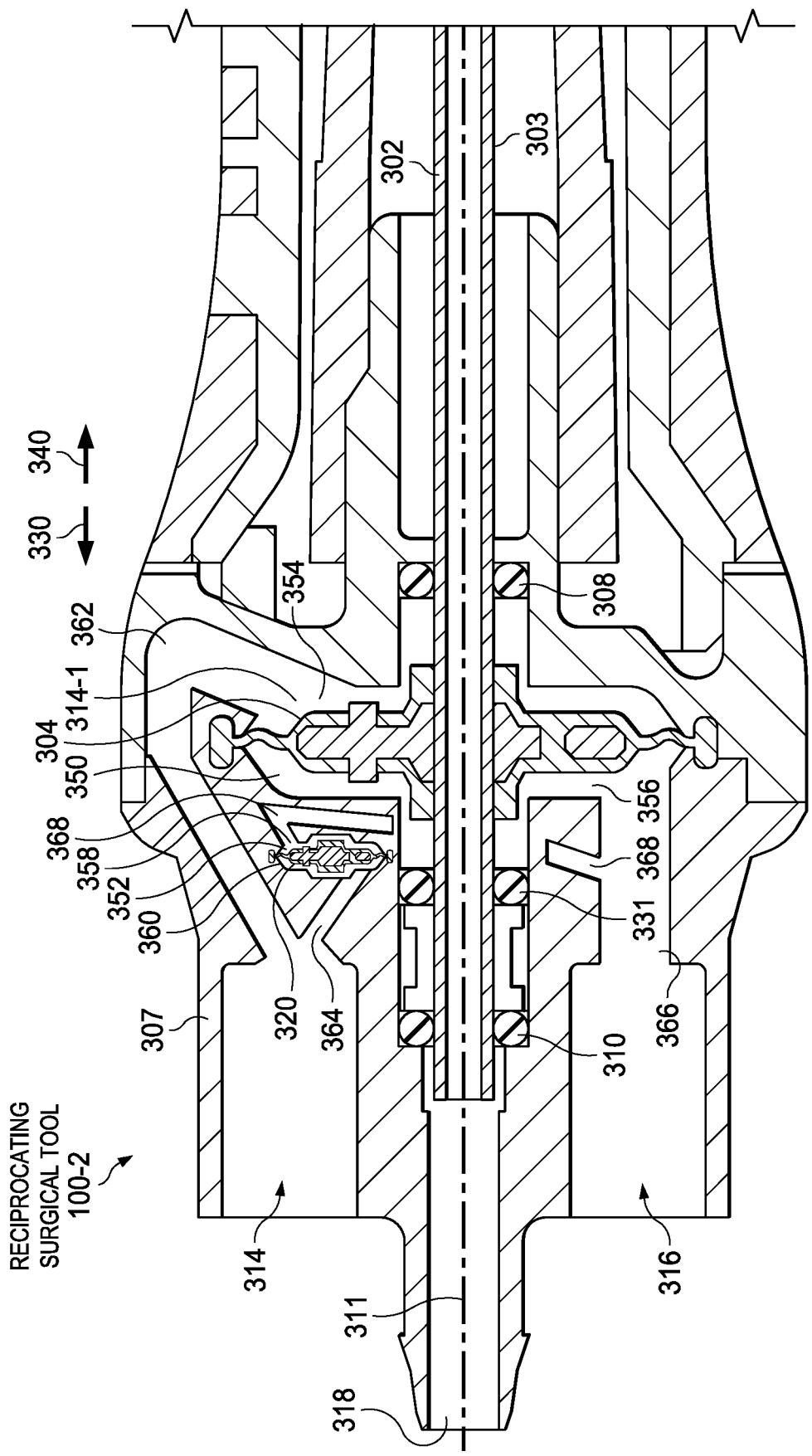
FIG. 3B is a schematic diagram of a detail view of an example reciprocating surgical tool containing a diaphragm inertial damper.

The dimensions and position of the secondary mass 206 may be influenced by the relative density of the secondary mass 206 as compared to the primary mass. For example, if the secondary mass 206 is formed from a dense metal, such as steel, while the primary mass is formed from a less dense polymer, the dimensions of the secondary mass 206 and of the central chamber 207 may be smaller than the primary mass and corresponding chamber for the primary mass, respectively. FIG. 3B shows an example in which the density of the materials forming the primary mass and the secondary mass 206, resulting in a marked difference in sizes of the primary mass and the secondary mass 206.

Figure 2B:
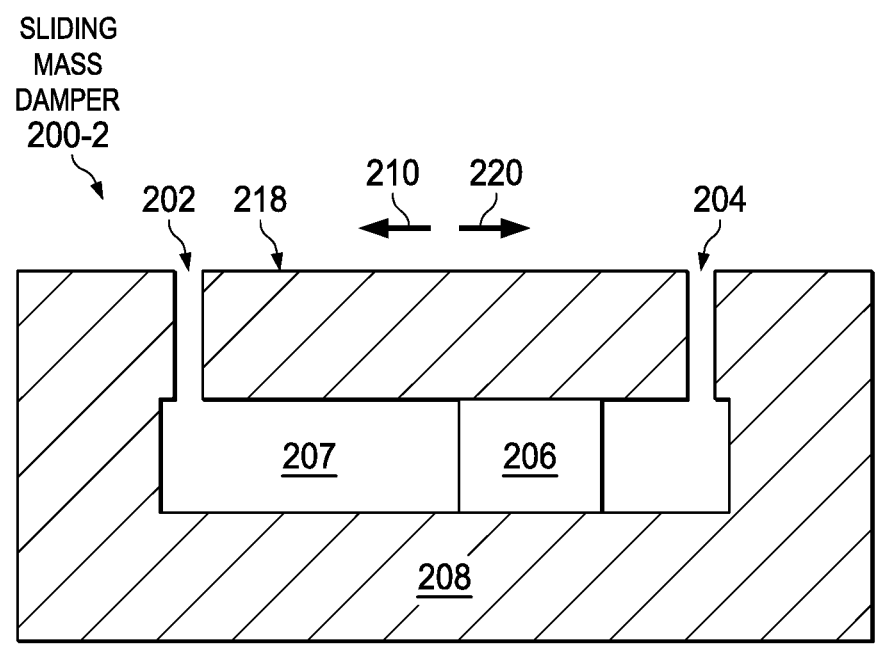
FIG. 2B is a schematic diagram of another example sliding mass damper.

Referring now to FIG. 2B, selected elements of an example of a sliding mass damper 200-2, which may be used as the inertial damper in a reciprocating surgical tool, such as reciprocating surgical tool 100 shown in FIG. 1, is illustrated. FIG. 2B is a schematic cross-sectional diagram and is not drawn to scale or perspective. The sliding mass damper 200-2 in FIG. 2B contains a housing body 208 having a first channel 202 and a second channel 204 formed therein, as well as a secondary mass 206. In the sliding mass damper 200-2 in FIG. 2B, an alternative configuration of the first channel 202 and the second channel 204 is depicted, as compared with the sliding mass damper 200-1 in FIG. 2A. Any of the elements, uses, operation, structure, or optional features of the sliding mass damper 200-2 in FIG. 2B may otherwise be the same as described above with respect to the sliding mass damper 200-1 in FIG. 2A.

In FIG. 2B, the first channel 202 and the second channel 204 are both located in the housing body 208 in positions roughly perpendicular to a first direction 210 and a second direction 220 that the secondary mass 206 moves. As shown in the sliding mass damper 200-2 in FIG. 2B, the first channel 202 and the second channel 204 are located at a common face 218 of the central chamber 207.

In FIG. 2B, the first channel 202 and the second channel 204 are in fluid communication with the central chamber 207, which is formed in the housing body 208 and in which the secondary mass 206 is able to reciprocate back and forth as a free mass in a first direction 210 and a second direction 220 opposing the first direction 210. When compressed air is applied to the central chamber 207 via the first channel 202, the secondary mass 206 will move in the second direction 220. When compressed air is applied to the central chamber 207 via the second channel 204, the secondary mass 206 will move in the first direction 210. As shown, sliding mass damper 200-2 is contemplated for use with dual pneumatic actuation inputs that are externally regulated and controlled. It is noted that sliding mass damper 200-2 may be dimensioned to handle various ranges of pressure and flow rates of the compressed air.

Although FIGS. 2A and 2B depict to potential implementations of the first channel 202 and the second channel 204, numerous other implementations are possible. For example, the first channel 202 and the second channel 204 may be located on opposite sides of the central chamber 207 in some implementations. In various implementations, the first channel 202 and the second channel 204 may form an oblique relative to the central chamber 207. Particularly, centerlines of one or both of the first channel 202 and the second channel 204 may form an oblique angle with the central line of symmetry 211 shown in FIG. 2A.

Figure 2C:
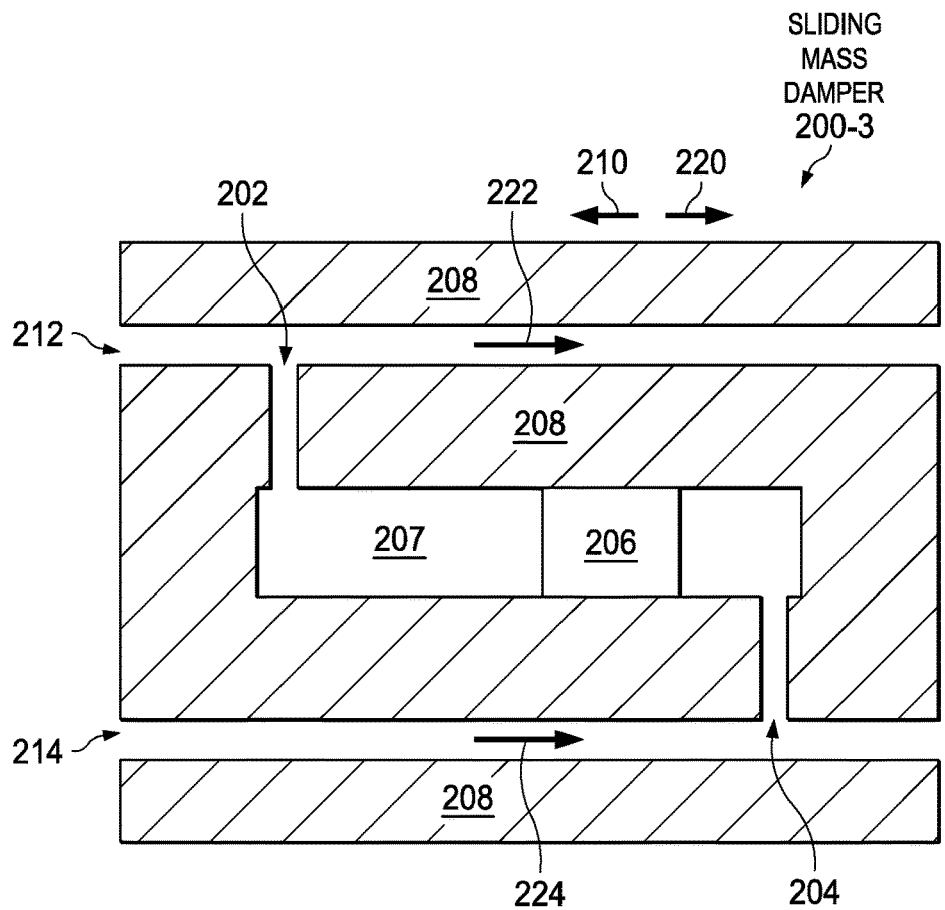
FIG. 2C is a schematic diagram of another example sliding mass damper.

Referring now to FIG. 2C, selected elements of an example of a sliding mass damper 200-3, which may be used as the inertial damper with a reciprocating surgical tool, such as reciprocating surgical tool 100 shown in FIG. 1, is illustrated. FIG. 2C is a schematic cross-sectional diagram and is not drawn to scale or perspective. The sliding mass damper 200-3 in FIG. 2C contains a housing body 208 having a first channel 202 and a second channel 204 formed therein, as well as a secondary mass 206 disposed in a central chamber 207 formed in the housing body 208.

The sliding mass damper 200-3 shown in FIG. 2C is an alternative implementation as compared to the sliding mass inertial dampers 200-2. The sliding mass damper 200-3. Specifically, the sliding mass inertial damper 200-3 may contain the housing body 208 integrally formed with or located within a reciprocating surgical tool, such as reciprocating surgical tool 100. Any of the elements, uses, operation, structure, or optional features of the sliding mass damper 200-3 may otherwise be the same as described above with respect to the sliding mass damper 200-1 shown in FIG. 2A. However, the sliding mass inertial damper 200-3 may contain the housing body 208 formed as an external device for a reciprocating surgical tool without inertial damping, as disclosed herein. Thus, the sliding mass inertial damper 200-3 may be used as an add-on or a separate device that is retroactively fitted with a conventional reciprocating surgical tool having dual pneumatic actuation inputs to provide inertial damping and the corresponding reduction in vibration.

Specifically, the sliding mass inertial damper 200-3 in FIG. 2C includes a pass-through channel 212 that transports compressed air along a first path 222 and a pass-through channel 214 that transports compressed air along a second path 224. The second path 224 is independent of the first path 222. In one example, the pass-through channel 212 may be connected using the first tube 110-1 (shown in FIG. 1), while the pass-through channel 214 may be connected using the second tube 110-2 (also shown in FIG. 1). The first tube 110-1 and the second tube 110-2 may be coupled at a proximal end thereof, respectively, to an external surgical device that controls the coordination of the pressurized gas supplied to the first and second tubs 110-1, 110-2. In some implementations, the external surgical device may be a surgical console, such as the Constellation® Vision System produced by Alcon Laboratories, Inc., located at 6201 South Freeway, Fort Worth, Tex. 76134. Distal ends of the first and second tubes 110-1, 110-2 may be coupled to respective first and second pass-through channels 212, 214. In this manner, the sliding mass damper 200-3 may be used with existing equipment that drives the reciprocating surgical tool.

At the output of the first and second pass-through channels 212, 214, a mechanical coupling (not shown) of the pass-through channels 212, 214 may provide a fixed external attachment to the reciprocating surgical tool, such that sufficient transfer of momentum between the reciprocating surgical tool and the sliding mass damper 200-3 occurs for inertial damping, as disclosed herein. For example, the sliding mass damper 200-3 may be particularly dimensioned to fit with a given model or implementation of the reciprocating surgical tool, such that the pass-through channels 212, 214 are aligned with corresponding pneumatic inlets of the reciprocating surgical tool. In some implementations, sliding mass damper 200-3 may include a third pass-through channel (not shown) to provide a connection for the aspiration line.

In FIG. 2C, the pass-through channel 212 is in fluid communication with the first channel 202 and the pass-through channel 214 is in fluid communication with the second channel 204. The first channel 202 and the second channel 204 are both located in the housing body 208 in positions roughly perpendicular to a first direction 210 and a second direction 220 in which the secondary mass 206 moves. The first direction 210 and the second direction 220 generally correspond to a direction of motion of the primary mass in the reciprocating surgical tool. It is noted that different orientations of the pass-through channel 212 and the pass-through channel 214 may be used in different implementations of the sliding mass damper 200-3. Further, in other implementations, the first and second directions 210, 220 may be parallel but offset to the motion of the primary mass; angularly offset from a direction of motion of the primary mass; or otherwise oriented in a manner unrelated to the direction of movement of the primary mass.

In FIG. 2C, the first channel 202 and the second channel 204 are in fluid communication with the central chamber 207, which is formed in the housing body 208, and in which the secondary mass 206 is able to reciprocate back and forth as a free mass in the first direction 210 and the second direction 220, opposite the first direction 210. When compressed air is applied to the central chamber 207 via the first channel 202, the secondary mass 206 moves in the second direction 220. When compressed air is applied to the central chamber 207 via the second channel 204, the secondary mass 206 moves in the first direction 210. As shown, sliding mass damper 200-3 is contemplated for use with dual pneumatic actuation inputs that are externally regulated and controlled. It is noted that sliding mass damper 200-3 may be dimensioned to handle various ranges of pressure and flow rates of the compressed air.

Figure 2D:
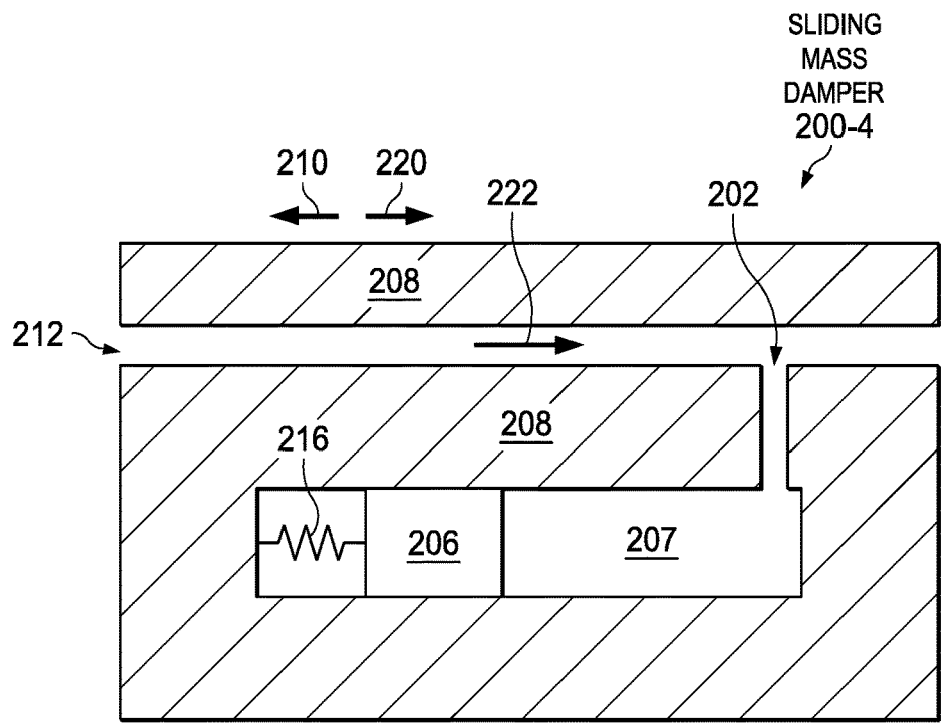
FIG. 2D is a schematic diagram of an additional example sliding mass damper.

Referring now to FIG. 2D, selected elements of an example of a sliding mass damper 200-4 is illustrated. The sliding mass damper 200-4 may be used as the inertial damper with a reciprocating surgical tool. FIG. 2C is a schematic cross-sectional diagram and is not drawn to scale or perspective. The sliding mass damper 200-4 in FIG. 2D contains a housing body 208 having a first channel 202 and a central chamber 207 formed therein. The sliding mass damper 200-4 also includes a secondary mass 206 disposed in the central chamber 207 and reciprocable therein. The sliding mass damper 200-4 shown in FIG. 2D is an alternative implementation in contrast to the sliding mass damper 200-3 shown in FIG. 2C. Specifically, the sliding mass damper 200-4 may be used with, or contained in, a reciprocating surgical probe that is implemented to receive a single pneumatic actuation input (for actuation in one direction) and includes a mechanical spring (for return in the reverse direction). Any of the elements, uses, operation, structure, or optional features of the sliding mass damper 200-4 may otherwise be the same as described above with respect to the sliding mass damper 200-3 shown in FIG. 2C. Accordingly, the sliding mass inertial damper 200-4 may contain the housing body 208 formed as an external device for a reciprocating surgical tool without inertial damping, as disclosed herein. Thus, the sliding mass inertial damper 200-4 may be used as an add-on or a separate device that is retroactively fitted with a conventional reciprocating surgical tool having a single pneumatic actuation input to provide inertial damping and the corresponding reduction in vibration.

Specifically, the sliding mass inertial damper 200-4 includes a pass-through channel 212 that transports a compressed gas (e.g., compressed air) along a first path 222. In one example, the pass-through channel 212 may be connected using the first tube 110-1. In this manner, the sliding mass damper 200-4 may be used with existing equipment that drives the reciprocating surgical tool, such as, for example, reciprocating surgical tool 100 shown in FIG. 1. A pneumatic tube, similar to the first tube 110-1 or the second tube 110-2, may be coupled at a proximal end to an external surgical device that controls application of pressurized gas to a reciprocating surgical tool. In some instances, the external surgical device may be a surgical console, as described above, for example. A distal end of the pneumatic tube may be coupled to the pass through channel 212.

At the output of the pass-through channel 212, a mechanical coupling (not shown) of the pass-through channel 212 may provide a fixed external attachment to the reciprocating surgical tool, such that sufficient transfer of momentum between the reciprocating surgical tool and the sliding mass damper 200-4 occurs for inertial damping, as disclosed herein. For example, the sliding mass damper 200-4 may be particularly dimensioned to fit with a given model or implementation of the reciprocating surgical tool, such that the pass-through channel 212 is aligned with corresponding pneumatic inlet of the reciprocating surgical tool. In some implementations, sliding mass damper 200-4 may include a second pass-through channel (not shown) to provide a connection for the aspiration line.

In FIG. 2D, the pass-through channel 212 is in fluid communication with the first channel 202. The first channel 202 is located in the housing body 208 in a position roughly perpendicular to a first direction 210 and a second direction 220 in which the secondary mass 206 moves. The first direction 210 and the second direction 220 generally correspond to a direction of motion of the primary mass in the reciprocating surgical tool. It is noted that different orientations of the pass-through channel 212 may be used in different implementations of the sliding mass damper 200-4. Further, in other implementations, the first and second directions 210, 220 may be parallel but offset to the motion of the primary mass of the reciprocating surgical tool; angularly offset from a direction of motion of the primary mass; or otherwise oriented in a manner unrelated to the direction of movement of the primary mass.

In FIG. 2D, the first channel 202 is in fluid communication with the central chamber 207, which is formed in the housing body 208. The secondary mass 206 is disposed within and is able to reciprocate back and forth as a free mass in a first direction 210 and a second direction 220, opposite the first direction 210, within the central chamber 207. When compressed gas, such as compressed air, is applied to the central chamber 207 via the first channel 202, the secondary mass 206 moves in the first direction 210. As a result, a mechanical spring 216 is compressed. When the pneumatic pressure of the pressurized gas is removed, the compressed mechanical spring 216 expands to move the secondary mass 206 in the second direction 220. As shown, sliding mass damper 200-4 is contemplated for use with a single pneumatic actuation input that is externally regulated and controlled. It is noted that sliding mass damper 200-4 may be dimensioned to handle various ranges of pressure and flow rates of the compressed air. Although a particular orientation of movement of the secondary mass 206, with respect to the first channel 202 and the mechanical spring 216 are shown, it will be understood that in different implementations, different orientations and arrangements may result in a reciprocating motion of the secondary mass.

FIG. 3A illustrates a cross-sectional view of a reciprocating surgical tool 100-1 containing a diaphragm inertial damper 306. FIG. 3A is not necessarily drawn to scale or perspective. As shown in FIG. 3A, certain aspects of the reciprocating surgical tool 100-1 may be rotationally symmetric about a central axis 311. In FIG. 3A, the reciprocating surgical tool 100-1 may be similar to the ULTRAVIT® surgical probe, discussed above. Similar to the ULTRAVIT® surgical probe, the reciprocating surgical tool 100-1 is a vitrectomy probe that uses dual pneumatic actuation of a reciprocating cutter 302. The reciprocating cutter 302 includes a tube 303 and a cutter tool 305. In the example shown, the distal portion 305 is received into a lumen 309 of the tube 303. However, in other instances, the tube 303 and the distal portion 305 may be a single, unitary piece. In still other implementations, the distal portion 305 and the tube 303 may be joined in any desired manner.

The distal portion 305 of the reciprocating cutter 302 includes a lumen 313 and is movable within an outer tube 315 that is fixed to a housing body 307. The lumen 309 and lumen 313 fluidly communicate with port 318 to collectively define an aspiration path through which aspirated material is transported through and out of the reciprocating surgical tool 100-1. The outer tube 315 includes a closed distal end 319 and a port 317 formed in a sidewall 321 of the outer tube 315. Material is permitted to enter the outer tube 315 through the port 317 to be severed by the distal end 305 as the distal end 305 reciprocates. Thus, the distal end 305 and the outer tube 315 cooperate to cut material in a guillotine-type of manner. The severed material is aspirated from the reciprocating surgical tool 100-1 via the lumen 313 of the distal portion 305 and lumen 309 of the tube 303.

In FIG. 3A, the reciprocating surgical tool 100-1 is showing having a first channel 314 and a second channel 316, which may receive a pneumatic connector or a fitting. For example, first channel 314 may receive a first tube through which pneumatic pressure may be communicated (e.g., the first tube 110-1 shown in FIG. 1), while second channel 316 may receive a second tube through which a pneumatic pressure may be communicated (e.g., the second tube 100-2 also shown in FIG. 1. Accordingly, the first channel 314 and the second channel 316 may represent two independent compressed air channels through which the compressed air is received in order to facilitate the dual pneumatic actuation described previously.

As shown in FIG. 3A, in addition to the diaphragm inertial damper 306, the reciprocating surgical tool 100-1 also includes a primary diaphragm 304. In the illustrated example, an outer periphery of the primary diaphragm is fixed to a housing body 307, while an inner periphery of the primary diaphragm 304 is fixed to the tube 303 of the reciprocating cutter 302. The reciprocating cutter 302 and the primary diaphragm 304 together form the primary mass. The primary diaphragm 304 is annularly disposed around and centered on the central axis 311. The central axis 311 also defines a central axis of the reciprocating cutter 302. An underpressure or a vacuum is applied to the port 318, lumen 309, and lumen 313 so as to draw aspirated material out of the reciprocating surgical tool 100-1. The distal cutting portion 305 can cut small portions of the vitreous while the cutting tool 302 reciprocates within the outer tube 315 past the port 317 in a first direction 330 and a second direction 340 that are both parallel with the central axis 311.

When a vacuum is applied to the port 318, material, such cut vitreous, may pass through the lumens 309 and 313 of the reciprocating cutter 302 and exit the reciprocating surgical tool 100-1. The vacuum applied via port 318 may be confined to the reciprocating cutter 302 through the use of one or more seals, such as annular seal 310, which may be, for example, an O-ring seal. Other implementations may provide alternative structures to allow removal of material from the reciprocating surgical tool 100-1.

In some implementations, the housing body 307 of the reciprocating surgical tool 100-1 may be a single, integrally formed component. In other implementations, the housing body 307 may be formed from two or more separate components. As explained above, the primary diaphragm 304 may be annularly fixed to the housing body 307 at an outer diameter or periphery of the primary diaphragm 304, as depicted. In other implementations, the primary diaphragm 304 may be otherwise fixed to the housing body 307. In the depicted implementation, the reciprocating cutter 302 extends through a central opening formed in the primary diaphragm 304 and is fixed to the inner periphery of the primary diaphragm 304. Various methods may be used to fix the reciprocating cutter 302 to the primary diaphragm 304. Accordingly, a movement of the primary diaphragm 304 causes a corresponding movement of the reciprocating cutter 302. When the primary diaphragm 304 moves in the first direction 330, the reciprocating cutter 302 moves in the first direction 330. When the primary diaphragm 304 moves in the second direction 340, the reciprocating cutter 302 moves in the second direction 340.

The reciprocating surgical tool 100-1 also contains a diaphragm inertial damper 306 that is annularly disposed around and centered on the central axis 311. The diaphragm inertial damper 306 represents a secondary diaphragm and includes a central opening through which the reciprocating cutter 302 extends. A seal 312 of the diaphragm inertial damper 306 is disposed between the diaphragm inertial damper 306 and the tube 303 and forms a low friction seal that permits to the tube 303 to move relative to the diaphragm inertial damper 306 with low friction.

The sliding seal 312 and the diaphragm inertial damper 306 together form the secondary mass of the reciprocating surgical tool 100-1. The diaphragm inertial damper 306 may be annularly fixed to the housing body 307 at an outer diameter or periphery of the diaphragm inertial damper 306, as depicted in a similar manner as the primary diaphragm 304. In various implementations, the diaphragm inertial damper 306 may be otherwise fixed to the housing body 307.

In the depicted implementation, the seal 312 is annularly disposed around and forms a fluid seal against the tube 303 of the reciprocating cutter 302. The seal 312 enables the reciprocating cutter 302 to move freely in the first direction 330 and the second direction 340 independently of the diaphragm inertial damper 306. The seal 312 may accordingly be formed using a low friction material that is nonetheless sufficiently wear resistant to enable continuous operation. The seal 312 may be fixed to the diaphragm inertial damper 306 in any fashion. For example, the seal 312 may be adhered to the diaphragm inertial damper 306 with an adhesive, a weld, or, in other instances, the diaphragm inertial damper 306 and the seal 312 may be integrally formed together. Still further, the diaphragm inertial damper 306 and the seal 312 may be joined in any manner.

As shown in FIG. 3A, the primary diaphragm 304 is located in a chamber 323 which is divided by the primary diaphragm 304 and the diaphragm inertial damper 306 into three separate subchambers 324, 325, and 326. The subchambers 324 and 326 are in fluid communication with each other and with the first channel 324 via a passage 328. The subchamber 325—is in fluid communication with the second channel 316 via a passage 329. Seals 310 and 331 are disposed at a proximal end of the subchamber 324 and are disposed between the housing body 307 and the tube 303 to provide a fluid seal therebetween. In some instances, the seals provided by the seals 310 and 331 may be fluid-tight seals. In other instances, the seals provided by seals 310 and 331 may not be fluid tight. A seal 308 is disposed at a distal end of the subchamber 326 and between the housing body 307 and the tube 303 to forms a fluid seal therebetween. In some instances, the seal provided by the seal 308 may be a fluid-tight seal. In other instances, the seal provided by seal 308 may not be fluid tight. In some instances, any one or all of the seals 308, 310, and 331 may be an O-ring seal. In the illustrated example, two annular seals 310 and 331 are included to seal against the tube 303 of the reciprocating cutter 302. However, in other implementations, one, two, or any number of seals may be used.

As shown, when compressed air is supplied to the first channel 314, the compressed air flows into subchamber 324 and 326 via passage 328, causing the primary diaphragm 304 and the reciprocating cutter 302 to move in the first direction 330, and causing the diaphragm inertial damper 306 to move in the second direction 340. When compressed air is supplied to the second channel 316, the compressed air flows into subchamber 325 causing the primary diaphragm 304 and the cutting tool 302 to move in the second direction 340, and causing the diaphragm inertial damper 306 to move in the first direction 330. Thus, as compressed air (e.g., an air pressure pulse) is supplied to the subchambers 324 and 326 and the subchamber 325 in an alternating manner, the primary diaphragm 304 and cutting tool 302 reciprocate, while the diaphragm inertial damper 306 will counter-reciprocate. Thus, the diaphragm 304 and the diaphragm inertial damper 306 move opposite each other in response to the same pneumatic pressure pulse. As a result of the implementation of the reciprocating surgical tool 100-1 shown in FIG. 3A, the reciprocation of cutting tool 302 and the counter-reciprocation of the diaphragm inertial damper 306 occur at the same frequency because the same dual inlet compressed gas is used for both the primary diaphragm 304 and the diaphragm inertial damper 306. With the diaphragm 304 and the diaphragm inertial damper 306 moving in this manner, the momentum of each of the diaphragm 304 and the diaphragm inertial damper 306 substantially cancel out each, reducing the amount of vibration generated by the reciprocating surgical tool 100-1 during operation.

In addition, the primary diaphragm 304 and the diaphragm inertial damper 306 may be similarly constructed. For example, the primary diaphragm 304 and the diaphragm inertial damper 306 may be constructed from similarly dense materials and/or have similar sizes. Consequently, the primary diaphragm 304 and the diaphragm inertial damper 306 may have comparable sizes and masses. As a result, both the primary diaphragm 304 and the diaphragm inertial damper 306 have a comparable momentum during reciprocation, because both will have a similar mass and a similar magnitude of velocity in response to actuation by the same gas pressure. Thus, when the primary diaphragm 304 and the cutting tool 302 are displaced, the combination of the primary diaphragm 304 and cutting tool 302 exhibit a momentum that may be similar in magnitude, but in an opposite direction, to the momentum exhibited by the diaphragm inertial damper 306. The momentums are opposite because the combination of the primary diaphragm 304 and the cutting tool 302 moves in a direction opposite to that of the diaphragm inertial damper 306 for the same pressure pulse of gas. As a result, a net momentum of the reciprocating surgical tool 100-1 may be reduced during operation. In some implementations, the net momentum may be zero; near zero; at least 80% lower, or at least 90% lower than the net momentum of a similarly constructed reciprocating surgical tool lacking the diaphragm inertial damper 306. The reduction in net momentum may result in reduced vibration of the reciprocating surgical tool 100-1 of FIG. 3A, and a corresponding reduction of the haptic vibration perceived by a surgeon holding the reciprocating surgical tool 100-1.

In some implementations, the primary mass formed from the primary diaphragm 304 and the cutting tool 302 and the secondary mass formed from the diaphragm inertial damper 306 and the sliding seal 312 may have similar masses. For example, the secondary mass may have at least 80% or at least 90% of the primary mass. Even when the secondary mass is somewhat larger than the primary mass, a useful reduction in the net momentum may be realized. In various implementations, both the primary mass and the secondary mass may be less than 100 mg; less than 200 mg; less than 500 mg; or less than 750 mg. However, the scope of the disclosure is not so limited. Rather, the primary mass and the secondary mass may be and desired or selected amount. For example, the masses may be larger than 750 mg or less than 100 mg. In one example that may be used in the reciprocating surgical tool, such as the example reciprocating surgical tool 100-1 of FIG. 3A, the cutting tool 302 may have a mass of about 350 mg. The diaphragm inertial damper 306 may include a stainless steel disc having a diameter of 7.5 mm and a thickness of 1 mm, resulting in a mass of about 350 mg. In general, the material, diameter, and thickness of the diaphragm inertial damper 306 may be varied to provide a mass similar to that of the primary diaphragm 304.

The reciprocating surgical tool 100-1 may further contain additional features that are not illustrated that nevertheless also facilitate formation or operation of the reciprocating surgical tool 100-1. For example, as explained above, the interface that exists between the seal 312 and the cutting tool 302 may be a low friction interface. Various interfaces contained in the reciprocating surgical tool 100-1 may support reciprocation of the cutting tool 302 and the seal 312 at a reciprocating frequency of up to 1,000 cycles per second. For example, an inner annular surface of the seal 312, an outer annular surface of the cutting tool 302, or both that form an interface with one another may be coated with a low-friction material, such as PTFE or a similar material.

Referring now to FIG. 3B, selected elements of another example reciprocating surgical tool 100-2 containing a diaphragm inertial damper 320 are shown. FIG. 3B is a central cross-section view of the reciprocating surgical tool 100-2, but is not necessarily drawn to scale or perspective. As shown in FIG. 3B, certain aspects of the reciprocating surgical tool 100-2 may by rotationally symmetric about a central axis 311. In FIG. 3B, the reciprocating surgical tool 100-2 may be similar to the ULTRAVIT® surgical probe, in that the reciprocating surgical tool 100-2 is a vitrectomy probe that uses dual pneumatic actuation of a reciprocating cutter 302.

In FIG. 3B, the reciprocating surgical tool 100-2 is similar in many aspects and features as described above with respect to the reciprocating surgical tool 100-1 in FIG. 3A. However, in the reciprocating surgical tool 100-2, instead of having a secondary mass that is disposed around the central axis 311 and is penetrated by the cutting tool 302, the diaphragm inertial damper 320 is positioned away from the central axis in the housing body 307 and is not penetrated by the cutting tool 302. Furthermore, the primary diaphragm 304 and the reciprocating surgical tool 100-2 are not disposed in a common chamber formed within the housing body 307. Instead, the primary diaphragm is located in a first chamber 350, while the diaphragm inertial damper 320 is disposed within a second chamber 352. Accordingly, the reciprocating surgical tool 100-2 eliminates the need for a seal, similar to the seal 312 of the reciprocating surgical tool 100-1 shown in FIG. 3A. Furthermore, in the reciprocating surgical tool 100-2, the diaphragm inertial damper 320 may be formed from a denser material than the primary diaphragm 304 and may be dimensioned smaller than the primary diaphragm 304, as shown in the example implementation of FIG. 3B.

The reciprocating surgical tool 100-2 is showing having a first channel 314 and a second channel 316, which may receive a pneumatic connector or a fitting. For example, first channel 314 may receive the first tube 110-1, while second channel 316 may receive the second tube 100-2 (see FIG. 1). Accordingly, the first channel 314 and the second channel 316 may represent two independent compressed air channels through which the compressed air is received in order to facilitate the dual pneumatic actuation described previously.

As shown in FIG. 3B, A primary diaphragm 304 may be annularly fixed to the housing body 307 at an outer diameter of the primary diaphragm 304, as depicted. In various implementations, the primary diaphragm 304 may be otherwise fixed to the housing body 307. Particularly, in the example shown, an outer periphery of the primary diaphragm 304 is fixed to the housing body 307. A tube 303 of a cutting tool 302 extends through a central opening formed in the primary diaphragm 304 and is secured to an inner periphery of the primary diaphragm 304. Various methods may be used to fix the cutting tool 302 to the primary diaphragm 304. Accordingly, a movement of the primary diaphragm 304 causes a corresponding movement of the cutting tool 302. When the primary diaphragm 304 moves in the first direction 330, the cutting tool 302 moves in the first direction 330. When the primary diaphragm 304 moves in the second direction 340, the cutting tool 302 moves in the second direction 340

The cutting tool 302 and primary diaphragm 304 together form the primary mass. The primary diaphragm 304 is annularly disposed around and centered on the central axis 311, which also forms a center of the cutting tool 302. As explained above, the cutting tool 302 defines a passage 309 through which material is aspirated. The passage 309 is in fluid communication with port 318, which may receive an aspiration line that applies underpressure or a vacuum, as described previously.

The diaphragm inertial damper 320 is disposed separately from the primary diaphragm 304 and cutting tool 302. The diaphragm inertial damper 320 represents a secondary diaphragm that forms the secondary mass of the reciprocating surgical tool 100-2. The diaphragm inertial damper 320 may be annularly fixed to the housing body 307 at an outer diameter of the diaphragm inertial damper 320, as depicted in a similar manner as the primary diaphragm 304. In various implementations, the diaphragm inertial damper 320 may be otherwise fixed to the housing body 307. As shown, the diaphragm inertial damper 320 may be smaller (and in some instances significantly smaller) in size than the primary diaphragm 304, because the diaphragm inertial damper 320 may be formed using a denser material. For example, when the primary diaphragm 304 and/or the cutting tool 302 are formed using polymer materials or a relatively lightweight metal, such as aluminum, the diaphragm inertial damper 320 may be formed using a heavier metal, such as steel, and still have a comparable mass to counteract the momentum of the primary diaphragm 304 and the cutting tool 302.

The primary diaphragm 304 divides the first chamber 350 into a first subchamber 354 and a second subchamber 356. The diaphragm inertial damper 320 divides the second chamber 352 into a third subchamber 358 and a fourth subchamber 360. Passages link the first and second chambers 350 and 352 so as move the primary diaphragm 304 and the diaphragm inertial damper 320 in offsetting directions so as to provide offsetting momentum during operation of the reciprocating surgical tool 100-2. A first passage 362 provides fluid communication between the first channel 314 and the first subchamber 354, and a second passage 364 provides fluid communication between the first channel 314 and the fourth subchamber 360. Additionally, a third passage 366 provides fluid communication between the second channel 316 and the second subchamber 356. A fourth passage 368 provides fluid communication between the second channel 316 and the third subchamber 358. In the cross-section of FIG. 3A, the passage 368 is shown as being two, disconnected parts. However, the two parts form one continuous passage, because the passage 368 is routed through the housing body 307 around the first chamber 350. Thus, as pneumatic pressure is applied via the first channel 314, the pneumatic pressure travels through the first passage 362, into the first subchamber 354, and displaces the primary diaphragm 304 and the cutting tool 302 in the first direction 330. At the same time, the pneumatic pressure from the first channel 314 is communicated through the second passage 364 and into the fourth subchamber 360 and displaces the diaphragm inertial damper 320 in the second direction 340 opposite the first direction. Consequently, when pneumatic pressure is applied to the first channel 314, the primary diaphragm 304 and the diaphragm inertial damper 320 move in opposing directions at the same time. Pneumatic pressure applied to the second channel 316 is communicated through the third passage 366 and into the second subchamber 356 where the pneumatic pressure displaces the primary diaphragm 304 and the cutting tool 302 in the second direction 340. At the same time, the pneumatic pressure from the second channel 316 is transmitted to the third subchamber 358 via the fourth passage 368 where the pneumatic pressure displaces the diaphragm inertial damper 320 in the first direction. As a result, when pneumatic pressure is applied to the second channel 316, the primary diaphragm 304 and the diaphragm inertial damper 320 again move in opposing directions at the same time. Thus, as pulses of pneumatic pressure are alternately applied to the first port 314 and the second port 316, the primary diaphragm 304 and the diaphragm inertial damper 320 are made to reciprocate in opposing directions. That is, the primary diaphragm 304 and cutting tool 302 reciprocate, while the diaphragm inertial damper 320 counter reciprocates. The reciprocation of the cutting tool 302 and the counter-reciprocation of the diaphragm inertial damper 320 occur at the same frequency because pneumatic pressure pulse are used to actuate both the primary diaphragm 304 and the diaphragm inertial damper 320 simultaneously.

In the implementation depicted in FIG. 3B and as explained above, the passage 309 of the cutting tool 302 is in fluid communication with a port 318. When a vacuum is applied to the port 318, material, such cut vitreous, may pass through the passage 309 of the cutting tool 302 and exit the reciprocating surgical tool 100-2. The vacuum applied via port 318 may be confined to the cutting tool 302 through the use of one or more seals, such as annular seal 310, which may be an O-ring seal. Other implementations may provide alternative structures to allow removal of material from the reciprocating surgical tool 100-2.

The housing body 307 of the reciprocating surgical tool 100-2 may be a single, integrally formed component. In other implementations, the housing body 307 may be formed from two or more separate components.

As noted, despite having different physical dimensions, the primary diaphragm 304 and the diaphragm inertial damper 320 may be constructed to have a comparable mass. For example, the primary diaphragm 304 and the diaphragm inertial damper 320 may be formed from materials having different densities. As a result, both the primary diaphragm 304 and the diaphragm inertial damper 320 generate a comparable momentum during reciprocation, because both will have a similar mass. Thus, during operation, the combination of the primary diaphragm 304 and the cutting tool 302 possess a momentum that may be similar in magnitude, but opposite in direction to the momentum possessed by the diaphragm inertial damper 320, because of the reverse direction of motion. Thus, the diaphragm inertial damper 320 may be considered to have a counter-momentum to that of the combination of the primary diaphragm 304 and the cutting tool 302 that is the same or almost the same in magnitude. As a result, a net momentum of the reciprocating surgical tool 100-2 may be reduced. In some implementation, the net momentum may be zero; near zero; at least 80% lower; or at least 90% lower than the net momentum of a similarly constructed reciprocating surgical tool lacking the diaphragm inertial damper 320. The reduction in net momentum may result in reduced vibration of the reciprocating surgical tool 100-2 of FIG. 3B, and a corresponding reduction of the haptic vibration perceived by a surgeon holding the reciprocating surgical tool 100-2.

In some implementations, the primary mass formed by the primary diaphragm 304 and the cutting tool 302 and the secondary mass formed by the diaphragm inertial damper 320 may be similar or comparable in size. For example, the secondary mass may be at least 80% or at least 90% of the primary mass. Even when the secondary mass is somewhat larger than the primary mass, a useful reduction in the net momentum may be realized. In various implementations, both the primary mass and the secondary mass may be less than 100 mg; less than 200 mg; less than 500 mg; or less than 750 mg. However, the scope of the disclosure is not so limited. Rather, the primary mass and the secondary mass may be and desired or selected amount. For example, the masses may be larger than 750 mg or less than 100 mg. In one example that may be used in the reciprocating surgical, such as the example reciprocating surgical tool 100-2 of FIG. 3B, the cutting tool 302 may have a mass of about 350 mg. The diaphragm inertial damper 320 may include a stainless steel disc having a diameter of 7.5 mm and a thickness of 1 mm, resulting in a mass of about 350 mg. In general, the material, diameter, and thickness of the diaphragm inertial damper 320 may be varied to provide a mass similar to that of the primary diaphragm 304.

The reciprocating surgical tool 100-2 may further contain additional features that are not illustrated that nevertheless also facilitate formation or operation of the reciprocating surgical tool 100-2. Various interfaces contained in the reciprocating surgical tool 100-2 may support reciprocation of the cutting tool 302 at a reciprocating frequency of up to 1,000 cycles per second.

A diaphragm inertial damper, such as diaphragm inertial damper 306 or 320 may be incorporated in various reciprocating surgical tools 100 by applying the principles described herein and as illustrated by the examples shown in FIGS. 3A and 3B. In addition, a sliding mass damper, such as sliding mass damper 200-1 of FIG. 2A; or sliding mass damper 200-2 of FIG. 2B; or sliding mass damper 200-3 of FIG. 2C; or sliding mass damper 200-4 of FIG. 2D; or another inertial damper containing another type of actuator, may be incorporated in another reciprocating surgical tool 100 by applying the principles described herein in connection with FIGS. 3A and 3B. For example, a sliding mass damper may be used in place of diaphragm inertial damper 306 or 320 in a reciprocating surgical tool similar to reciprocating surgical tools 100-1 or 100-2.

Figure 4:
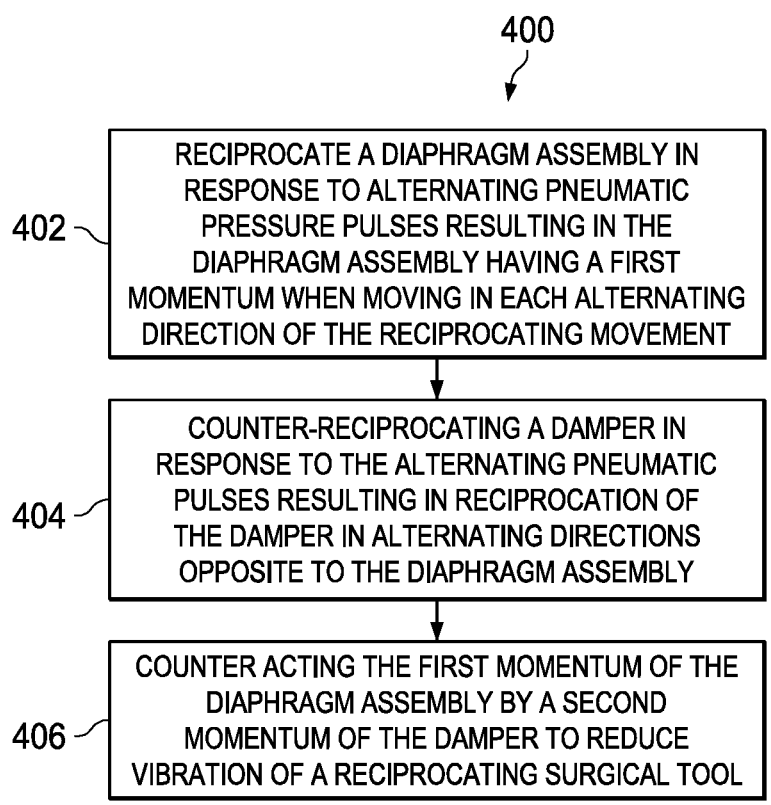
FIG. 4 is a flow chart of an example method for operating a reciprocating surgical tool with an inertial damper during ophthalmic surgery.

FIG. 4 provides a flow chart of an example method 400 for operating a reciprocating surgical tool 100, as described herein. Certain operations described in the method 400 may be optional and/or may be rearranged in different implementations. The method 400 may be performed using any implementation of the reciprocating surgical tools, such as reciprocating surgical tools 100-1 and 100-2, described herein.

At step 402, a diaphragm assembly disposed in a reciprocating surgical tool is reciprocated in response to alternating pneumatic pressure pulses, the diaphragm assembly forming a primary mass and having a first momentum when moving in each alternating direction of the reciprocating movement. At step 404, a damper, also disposed in the reciprocating surgical tool, is counter-reciprocated in response to the same alternating pneumatic pressures by reciprocating the damper in the alternating directions opposite to the diaphragm assembly. The damper forms a secondary mass and has a second momentum less than or equal to the first momentum when moving in each of the alternating directions of the reciprocating movement. The second momentum is diametrically opposite to the first momentum of the diaphragm assembly such that, at step 406, the first momentum of the diaphragm assembly is counteracted by the second momentum of the damper to reduce the vibration of the reciprocating surgical tool. The diaphragm assembly may include a diaphragm, which may be similar to diaphragm 304, and a cutter tool, which may be similar to cutter tool 302. In various implementations, the first momentum may have about the same magnitude as the second momentum. In other implementations, the first momentum may have a magnitude that is at least 70% to 80%, at least 80% to 90%, or at least 90% to 100% of the second momentum. In some implementations, the first momentum may be larger than the second momentum, while, in other implementations, the second momentum may be larger than the first momentum. The reciprocation and counter-reciprocation of the primary mass and secondary mass, respectively, may diminish the overall vibration generated by the reciprocating surgical tool and haptically perceived by a surgeon holding the reciprocating surgical tool.

The above disclosed subject matter is to be considered illustrative and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A reciprocating surgical tool for use in ophthalmic surgery, comprising:
    a housing body
    a first channel formed in the housing body;
    a second channel formed in the housing body;
    a diaphragm assembly having a first mass and comprising:
        a first diaphragm; and
        a surgical cutter, the first diaphragm being actuated to reciprocate in a first direction and a second direction in response to alternating pneumatic pressures applied to the first diaphragm via the first channel to cause the diaphragm assembly to be displaced in the first direction and via the second channel to cause the diaphragm assembly to be displaced in the second direction opposite the first direction, the diaphragm assembly having a first momentum when being displaced in the first direction and the second direction; and
    an inertial damper being actuated to reciprocate in the first direction and the second direction in response to the alternating pneumatic pressures applied to the inertial damper via the first channel to cause the inertial damper to be displaced in the second direction and via the second channel to cause the inertial damper to be displaced in the first direction, the inertial damper having a second momentum less than or equal to the first momentum in magnitude when being displaced in the first direction and the second direction, the second momentum and the first momentum being diametrically opposite.

2. The reciprocating surgical tool of claim 1, wherein the alternating pneumatic pressure is supplied from an ophthalmic surgical system, the ophthalmic surgical system comprising:
    a dual-channel pneumatic actuator configured to provide the pneumatic pressure pulses to the first channel and to the second channel independently of each other; and
    an aspiration system configured to provide a vacuum to a passage extending through the surgical cutter.

3. The reciprocating surgical tool of claim 1, wherein the reciprocating surgical tool is a handheld surgical tool.

4. The reciprocating surgical tool of claim 3, wherein the handheld surgical tool is a vitrectomy probe.

5. The reciprocating surgical tool of claim 1, wherein the surgical cutter operates at a rate of up to 1,000 cutting cycles per second.

6. The reciprocating surgical tool of claim 1, wherein the inertial damper comprises a free mass that is configured to reciprocate in an enclosed channel formed in the housing body.

7. The reciprocating surgical tool of claim 1, wherein the inertial damper comprises a second diaphragm that is the same size as the first diaphragm.

8. The reciprocating surgical tool of claim 1, wherein the surgical cutter is fixed to the first diaphragm along a central axis thereof.

9. The reciprocating surgical tool of claim 1, wherein the inertial damper comprises a second diaphragm that is smaller in size than the first diaphragm.

10. The reciprocating surgical tool of claim 1, wherein the inertial damper comprises a metallic portion having a second mass that is less than or equal to the first mass.

* * * * *